United States Patent [19]

Vorbrueggen

[11] Patent Number: 4,554,363
[45] Date of Patent: Nov. 19, 1985

[54] PROCESS FOR THE PREPARATION OF CARBACYCLIN INTERMEDIATES

[75] Inventor: Helmut Vorbrueggen, Berlin, Fed. Rep. of Germany

[73] Assignee: Schering Aktiengesellschaft, Bergkamen, Fed. Rep. of Germany

[21] Appl. No.: 516,602

[22] PCT Filed: Oct. 14, 1982

[86] PCT No.: PCT/DE82/00205

§ 371 Date: Jun. 23, 1983

§ 102(e) Date: Jun. 23, 1983

[87] PCT Pub. No.: WO83/01449

PCT Pub. Date: Apr. 28, 1983

[30] Foreign Application Priority Data

Oct. 23, 1981 [DE] Fed. Rep. of Germany ....... 3142733

[51] Int. Cl.[4] .................... C07D 309/12; C07C 45/48
[52] U.S. Cl. ................................. 549/415; 568/346; 568/314; 556/406; 556/436; 549/4; 549/60; 549/66; 549/78; 549/214; 549/349; 549/359; 549/416; 549/417; 549/421; 549/476; 549/414; 549/479; 549/498; 546/14; 546/268; 546/296; 546/301; 546/302; 546/304
[58] Field of Search .............. 568/346, 314; 549/416, 549/415, 421, 214, 479, 60, 498, 66, 476, 78, 417, 4, 414, 359, 349; 556/436, 406; 546/268, 302, 14, 296, 301, 340

[56] References Cited

FOREIGN PATENT DOCUMENTS 2070596 9/1981 United Kingdom .

OTHER PUBLICATIONS

Valente et al., Carbohydrate Research, 90, 329–333 (1981).
Bestman et al., C.A., 92, 214991x (1980).

*Primary Examiner*—Nicky Chan
*Attorney, Agent, or Firm*—Millen & White

[57] ABSTRACT

Process for the preparation of bicyclic ketones containing blocked hydroxy groups, of general Formula I

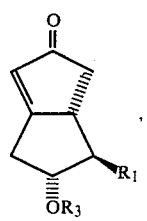

wherein $R_1$ is the residues —$CH_2OR_2$ wherein $R_2$ means benzyl, dimethyl-tert-butylsilyl, diphenyl-tert-butylsilyl, dimethylphenylsilyl, tribenzylsilyl, or tetrahydropyranyl,

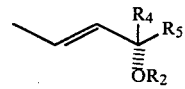

with $R_2$ having the meanings given above, $R_4$ meaning hydrogen or methyl, and $R_5$ meaning a straight-chain or branched-chain, saturated or unsaturated alkyl residue which can contain fluorine, chlorine, 1,2-methylene, 1,1-trimethylene, or methoxy substitutents, or a $CH_2$—X-Aryl residue with X meaning $CH_2$ or O and Aryl meaning phenyl or a heterocyclic residue, which residues can be substituted by methyl, methoxy, fluorine, chlorine, bromine, or trifluoromethyl, or

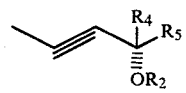

with the meanings for $R_2$, $R_4$, and $R_5$ as indicated above, and $R_3$ having the meanings set forth for $R_2$, it being possible for $R_3$ to be identical to $R_2$ or different from $R_2$ or to represent, jointly with $R_2$, the grouping

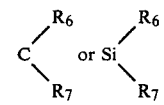

wherein $R_6$ and $R_7$ are the same or different and signify hydrogen, alkyl, cycloalkyl, characterized by reacting a keto acid containing blocked hydroxy groups, according to general Formula II

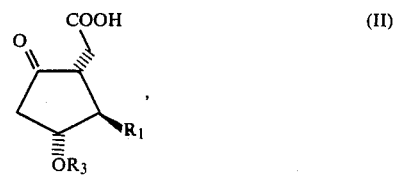

with triphenyl(phenyliminovinylidene)phosphorane and subsequently with alcohols.

8 Claims, No Drawings

PROCESS FOR THE PREPARATION OF CARBACYCLIN INTERMEDIATES

BACKGROUND OF THE INVENTION

The present invention concerns a process for the preparation of bicyclic ketones, which contain blocked hydroxy groups, from corresponding keto acids. All of the conventional processes for the production of carbacyclin intermediate stages, starting with intermediates from the Corey prostaglandin synthesis, especially the γ-lactones, not only proceed by way of many reaction stages (cf. DOS No. 2,912,409 or DOS No. 3,021,895) and yield undesirable by-products, but also demand very strict adherence to the reaction conditions [cf. P. A. Aristoff, J. Org. Chem. 46:1954 (1981)] for the internal Wittig reaction that takes place. According to P. A. Aristoff, hydroxy groups in γ-keto compounds blocked with tetrahydropyranyl (THP), for example, do not withstand more vigorous reaction conditions, such as, for example those described by H. J. Bestmann et al. in "Angew. Chemie" [Applied Chemistry] 92:856 (1980). The primary products are no longer the desired carbacyclin intermediates, but rather compounds of the type of PGA, due to β-elimination of the THP ether in the cyclopentane ring.

It has been discovered that the γ-keto acids, readily accessible from Corey lactones by alkaline opening and Jones oxidation of the γ-hydroxy acid, can be converted with good yields into the α,β-unsaturated ketones by reaction with triphenyl(phenyliminovinylidene)phosphorane. These ketones can be very easily converted into saturated carbacyclin intermediates by hydrogenation or hydride transfer with triethylammonium formate/5% palladium-carbon [cf. R. F. Heck et al., J. Org. Chem. 43:3985 (1978)].

SUMMARY OF THE INVENTION

Accordingly, the invention relates to a process for the preparation of bicyclic ketones containing blocked hydroxy groups, of general Formula I

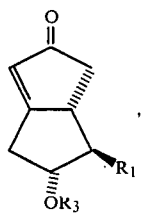

(I)

wherein $R_1$ is the residues —$CH_2OR_2$ wherein $R_2$ means benzyl, dimethyl-tert-butylsilyl, diphenyl-tert-butylsilyl, dimethylphenylsilyl, tribenzylsilyl, or tetrahydropyranyl,

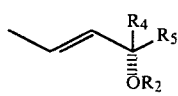

with $R_2$ having the meanings given above, $R_4$ meaning hydrogen or methyl, and $R_5$ meaning a straight-chain or branched-chain, saturated or unsaturated alkyl residue i.e., including alkenyl or alkynyl, which can contain fluorine, chlorine, 1,2-methylene, 1,1-trimethylene, or methoxy substituents, or a $CH_2$—X-Aryl residue with X meaning $CH_2$ or O and Aryl meaning phenyl or a heterocyclic residue, which residues can be substituted by methyl, methoxy, fluorine, chlorine, bromine, or trifluoromethyl, or

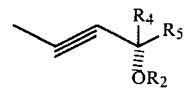

with the meanings for $R_2$, $R_4$, and $R_5$ as indicated above, and $R_3$ having the meanings set forth for $R_2$, it being possible for $R_3$ to be identical to $R_2$ or different from $R_2$ or to represent, jointly with $R_2$, the grouping

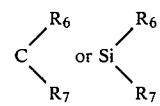

wherein $R_6$ and $R_7$ are the same or different and signify hydrogen, alkyl, cycloalkyl, characterized by reacting a keto acid containing blocked hydroxy groups, according to general Formula II

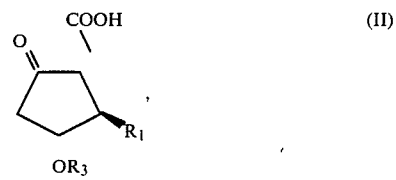

(II)

with triphenyl(phenyliminovinylidene)phosphorane and subsequently with alcohols.

DETAILED DISCUSSION

The reaction of the γ-keto acids II with triphenyl(phenyliminovinylidene)phosphorane is conducted with exclusion of moisture in aprotic solvents, such as ethyl acetate, toluene, ethylene chloride, acetonitrile, preferably in ethyl acetate or acetonitrile, at temperatures of 50°–150° C., normally at the boiling point of the respective solvent, within 1–5 hours. After concentration of the reaction mixture, the next step, without purification, is the reaction with alcohols within 5–20 hours in absolute, aprotic solvents, preferably in toluene.

Suitable alcohols for the above-described reaction are primarily n-alcohols of 1–4 carbon atoms, such as methanol, ethanol, n-propanol, isopropanol, n-butanol.

Suitable alkyl groups $R_5$ are straight- and branched-chain, saturated and unsaturated alkyl residues, preferably saturated ones of 1–10, especially 1–7 carbon atoms, which can, if desired, be substituted by optionally substituted phenyl, fluorine, chlorine, 1,2-methylene, 1,1-trimethylene, or methoxy. Examples are methyl, ethyl, propyl, butyl, isobutyl, tert-butyl, pentyl, hexyl, heptyl, octyl, butenyl, isobutenyl, propenyl, pentenyl, hexenyl, butynyl, pentynyl, benzyl, and p-chlorobenzyl.

Suitable heterocyclic groups (aryl) are 5- and 6-membered heterocycles, among which those having a hetero atom, e.g. nitrogen, oxygen, or sulfur, are especially preferred. Examples are 2-furyl, 2-thienyl, 3-thienyl, 2-pyridyl, 3-pyridyl, 4-pyridyl, and others.

The alkyl groups $R_6$ and $R_7$ are straight-chain or branched and contain 1–4 carbon atoms, such as, for example, methyl, ethyl, propyl, isopropyl, butyl, isobutyl, tert-butyl.

The cycloalkyl groups $R_6$ and $R_7$ can contain in the ring 4–10, preferably 5 and 6 carbon atoms. The rings can be substituted by alkyl groups of 1–4 carbon atoms. Examples are cyclopentyl, cyclohexyl, methylcyclohexyl, and adamantyl.

The carbacyclin intermediates prepared according to the process of this invention represent starting compounds for pharmacologically active prostacyclins.

EXAMPLE 1

7α-(Tetrahydropyran-2-yloxy)-6β-(benzyloxymethylene)bicyclo[3.3.0]oct-1-en-3-one 3.5 g (about 10 millimoles) of crude 2α-carboxymethyl-3β-benzyloxymethyl-4α-(tetrahydropyran-2-yloxy)cyclopentanone was boiled in 80 ml of dry ethyl acetate with 3.8 (10 mmol) of triphenyl(phenyliminovinylidene)phosphorane under exclusion of moisture for 3 hours, concentrated, and the residue refluxed in 40 ml of toluene and 2.5 ml of absolute ethanol for 12 hours. The crude product was evaporated and extracted repeatedly with hexane in the hot state with the addition of acetone, thus obtaining 6.4 g of a crude hexane extract which was chromatographed on 300 g of silica gel with toluene-ethyl acetate 19:1 and 9:1, yielding, besides 0.72 g (about 20%) of starting lactone, 1.02 g (31.3% total yield) of final product.

The starting material for the above title compound was prepared as follows:

2α-Carboxymethyl-3β-benzyloxymethylene-3α-(tetrahydropyran-2-yloxy)cyclopentanone A solution of 3.67 g (9.53 mmol) of 7α-(tetrahydropyran-2-yloxy)-6β-(benzyloxymethyl)-2-oxabicyclo[3.3.0]octan-3-one and 35 ml of 1 NaOH in 35 ml of ether was agitated at 25° C. for 2.5 hours; the aqueous phase was separated, cooled with ice, and gently acidified to pH=4–5 with ice-cold citric acid. After extraction with 2×20 ml of ice-cold $CH_2Cl_2$, the mixture was rapidly filtered over a small amount of $Na_2SO_4$ and diluted with 40 ml of acetone. After cooling to −30° C., about 4 ml of Jones reagent was added during 10 minutes. After 2.5 hours at −30° C., another 1 ml of Jones reagent was added, and the mixture was finally combined with 5 ml of isopropanol. After another 5 minutes at −30° C., about 70 ml of ice water was added and the mixture extracted with 3×50 ml of $CH_2Cl_2$. After washing with saturated NaCl solution, drying ($Na_2SO_4$), and concentration, 3.5 g of crude product was thus obtained, which was further processed immediately.

EXAMPLE 2

7α-(Tetrahydropyran-2-yloxy)-6β-[3'α-(tetrahydropyran-2-yloxy)-4'-methyltrans-1'-octenyl]bicyclo[3.3.0]oct-1-en-3-one 2.22 g (about 4.76 mmol) of crude 2α-(carboxymethylene)-3β-[3'α-(tetrahydropyran-2-yloxy)-4'-methyltrans-1'-octenyl]-4α-(tetrahydropyran-2-yloxy)cyclopentanone was refluxed with 1.97 g (5.23 mmol) of triphenyl(phenyliminovinylidene)phosphorane in 43 ml of dry ethyl acetate for 3 hours, evaporated, and the residue boiled with 25 ml of toluene and 1.5 ml of ethanol for 12 hours. After evaporation and extraction with boiling hexane and a small amount of acetone, the residue (3.81 g) was chromatographed on 200 g of silica gel with toluene-ethyl acetate 9:1 and 82, thus obtaining 1.1 g (about 50% total yield) of final product.

The starting material for the above title compound was produced as follows:

2α-(Carboxymethylene)-3β-[3'α-(tetrahydropyran-2-yloxy)-4'-methyltrans-1'-octenyl]-4α-(tetrahydropyran-2-yloxy)cyclopentanone A solution of 2.25 g (5 mmol) of 7α-(tetrahydropyran-2-yloxy)-6β-[3'α-(tetrahydropyran-2-yloxy)-4'-methyl-trans-1'-octenyl]-2-oxabicyclo[3.3.0]octan-3-one in 19 ml of ether was agitated for 18 hours overnight with 19 ml of 1N NaOH; the ether phase was agitated with 2 ml of 1N NaOH, and the alkaline phase was gently acidified at 0° C. to pH=4–5 with saturated citric acid solution. After extraction with 2×10 ml of ice-cold methylene chloride and drying ($Na_2SO_4$), the mixture was diluted with 21 ml of acetone and, at −30° C., 2.54 ml of Jones reagent was added dropwise thereto. After 2.5 hours at −30° C., 3 ml of isopropanol was added, the mixture was stirred for 5 minutes at −30° C., and combined with about 40 ml of ice water. After extraction with 3×50 ml of $CH_2Cl_2$, washing with saturated NaCl solution, and drying ($Na_2SO_4$), 2.22 g of crude title compound was obtained, which was further processed immediately.

EXAMPLE 3

7α-(Tetrahydropyran-2-yloxy)-6β-[3'α-(tetrahydropyran-2-yloxy)-4'-phenoxytrans-1'-butenyl]bicyclo[3.3.0]octan-1-en-3-one 2.63 g (about 5 mmol) of crude 2α-(carboxymethylene)-3β-[3'α-(tetrahydropyran-2-yloxy)-4'-phenoxytrans-1'-butenyl]-4α-(tetrahydropyran-2-yloxy)cyclopentanone was left standing with 2.07 g (5.5 mmol) of triphenyl(phenyliminovinylidene)phosphorane in 45 ml of dry ethyl acetate at 24° C. for 72 hours and then refluxed for 3 hours under exclusion of moisture, evaporated, and the residue boiled in 23 ml of absolute toluene with 1.43 ml of ethanol for 12 hours. After evaporation, dissolution in a small amount of acetone, and evaporation of the acetone with excess hexane, a hexane extract was obtained (3.52 g) which was chromatographed on 200 g of silica gel with toluene-ethyl acetate. Elution with 9:1 and 8:2 mixture yielded 0.96 g (41%) of the title compound which, in the system of toluene-ethyl acetate 2:1 was uniform as per thin-layer chromatography.

The starting material for the above title compound was prepared as set forth below:

2α-(Carboxymethylene)-3β-[3'α-(tetrahydropyran-2-yloxy)-4'-phenoxytrans-1'-butenyl]-4α-(tetrahydropyran-2-yloxy)cyclopentanone A solution of 2.36 g (5 mmol) of 7α-(tetrahydropyran-2-yloxy)-6β-[3'α-(tetrahydropyran-2-yloxy)-4'-phenoxy trans-1'-butenyl]-2-oxabicyclo[3.3.0]octan-3-one was agitated in 19 ml of ether for 17 hours with 18.55 ml of 1N NaOH. The phases were separated, and the ether phase was additionally extracted with a small amount of 1N NaOH. The combined alkaline-aqueous phase was acidified at 0° C. to pH=4–5 with ice-cold citric acid solution, and the aqueous solution was extracted with ice-cold methylene chloride. After filtration of the methylene chloride extracts over a layer of $Na_2SO_4$, the mixture was diluted with about 20 ml of acetone, cooled to −30° C., and 2.54 ml of Jones reagent was added dropwise. After 2.5 hours, at −30° C., 3 ml of isopropanol was added and the mixture stirred for another 5 minutes. About 50 ml of ice water was added to the reaction mixture, and the aqueous phase was extracted with 3×50 ml of methylene chloride. The organic phase was washed neutral with a small amount of saturated NaCl solution, dried (Na$_2$SO$_4$), and evaporated, thus obtaining 2.63 g of crude title compound.

I claim:

1. A process for the preparation of a bicyclic ketone containing blocked hydroxy groups of the formula

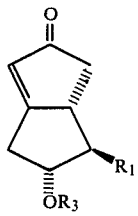

wherein
R$_1$ is
(a) —CH$_2$OR$_2$ wherein R$_2$ is benzyl, dimethyl-tert-butyl-silyl, diphenyl-tert-butylsilyl, dimethylphenylsilyl, tribenzylsilyl, or tetrahydropyranyl;
(b)

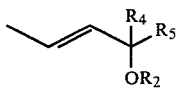

wherein R$_2$ is as defined above, R$_4$ is hydrogen or methyl, and R$_5$ is alkyl, alkenyl or alkynyl, each optionally substituted by fluorine, chlorine, 1,2-methylene, 1,1-trimethylene, or methoxy, or R$_5$ is benzyl or p-chlorobenzyl;
(c) —CH$_2$—X-Aryl wherein X is CH$_2$ or O and Aryl is phenyl or an aromatic heterocyclic ring of 5 or 6 ring atoms one of which is a hetero atom which is O, N or S bound to X via a 2-, 3- or 4-position of the heterocyclic ring, each of which aryl groups optionally is substituted by methyl, methoxy, fluorine, chlorine, bromine, or trifluoromethyl; or
(d)

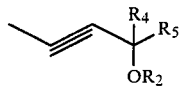

wherein R$_2$, R$_4$, and R$_5$ are as defined above; and R$_3$ has one of the meanings given for R$_2$, it being possible for R$_3$ to be identical to R$_2$ or different from R$_2$ or to represent, jointly with R$_2$, the grouping

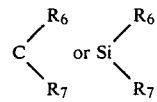

wherein R$_6$ and R$_7$ are the same or different and each is hydrogen, alkyl, or cycloalkyl,
comprising reacting a keto acid containing blocked hydroxy groups of the formula

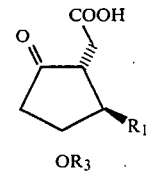

with triphenyl(phenyliminovinylidene)phosphorane in an aprotic solvent with the exclusion of moisture and then reacting the resultant product with an alcohol in an absolute, aprotic solvent.

2. A process of claim 1, wherein R$_3$ has one of the meanings given for R$_2$.

3. A process of claim 1, wherein the aprotic solvent is ethyl acetate, toluene, ethylene chloride or acetonitrile.

4. A process of claim 1, wherein the first step is conducted in ethyl acetate or acetonitrile and the second step is conducted in toluene.

5. A process of claim 1, wherein the first step is conducted at 50°–150° C.

6. A process of claim 1, wherein the alcohol in the second step is a C$_{1-4}$ alkanol.

7. A process of claim 1, wherein the R$_5$ group is alkyl of 1–10 carbon atoms.

8. A process of claim 1, wherein R$_5$ is methyl, ethyl, propyl, butyl, isobutyl, tert-butyl, pentyl, hexyl, heptyl, octyl, butenyl, isobutenyl, propenyl, pentenyl, hexenyl, butynyl, pentynyl, benzyl, or p-chlorobenzyl.

* * * * *